(12) United States Patent
Toth et al.

(10) Patent No.: US 10,350,015 B2
(45) Date of Patent: *Jul. 16, 2019

(54) TOOL MEMORY-BASED SOFTWARE UPGRADES FOR ROBOTIC SURGERY

(71) Applicant: Intuitive Surgical Operations, Inc., Sunnyvale, CA (US)

(72) Inventors: Gregory K. Toth, Los Altos, CA (US); Nitish Swarup, Sunnyvale, CA (US); Thomas R. Nixon, San Jose, CA (US); David Q. Larkin, Menlo Park, CA (US); Steven J. Colton, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 15/147,171

(22) Filed: May 5, 2016

(65) Prior Publication Data
US 2016/0242859 A1    Aug. 25, 2016

Related U.S. Application Data

(63) Continuation of application No. 14/145,406, filed on Dec. 31, 2013, now Pat. No. 9,345,546, which is a
(Continued)

(51) Int. Cl.
*A61B 34/32* (2016.01)
*A61B 34/37* (2016.01)
(Continued)

(52) U.S. Cl.
CPC ............. *A61B 34/32* (2016.02); *A61B 34/30* (2016.02); *A61B 34/35* (2016.02); *A61B 34/37* (2016.02);
(Continued)

(58) Field of Classification Search
CPC ......... A61B 34/30; A61B 34/32; A61B 34/35; A61B 34/37; A61B 90/361;
(Continued)

(56) References Cited

U.S. PATENT DOCUMENTS

| 5,400,267 A | 3/1995 | Denen et al. |
| 5,771,553 A | 6/1998 | Sim et al. |

(Continued)

FOREIGN PATENT DOCUMENTS

| JP | S59232781 A | 12/1984 |
| JP | S6116295 U | 1/1986 |

(Continued)

OTHER PUBLICATIONS

Burghart Catherina et al., "On-line motion planning for medical applications," Proceedings of the 24th Annual Conference of the IEEE Industrial Electronics Society, Aug. 31-Sep. 4, 1998, vol. 4, pp. 2233-2238, IEEE.

(Continued)

*Primary Examiner* — Jerrah Edwards

(57) ABSTRACT

Robotic devices, systems, and methods for use in robotic surgery and other robotic applications, and/or medical instrument devices, systems, and methods includes both a reusable processor and a limited-use robotic tool or medical treatment probe. A memory the limited-use component includes machine readable code with data and/or programming instructions to be implemented by the processor. Programming of the processor can be updated by shipping of new data once downloaded by the processor from a component, subsequent components can take advantage of the updated processor without repeated downloading.

10 Claims, 8 Drawing Sheets

Related U.S. Application Data continuation of application No. 13/158,041, filed on Jun. 10, 2011, now Pat. No. 8,634,957, which is a continuation of application No. 12/114,082, filed on May 2, 2008, now Pat. No. 7,983,793, which is a continuation of application No. 10/839,727, filed on May 4, 2004, now Pat. No. 7,379,790.

(51) Int. Cl.
  *A61B 34/30* (2016.01)
  *A61B 34/35* (2016.01)
  *G16H 40/40* (2018.01)
  *A61B 17/00* (2006.01)
  *A61B 90/00* (2016.01)

(52) U.S. Cl.
  CPC ............ *G16H 40/40* (2018.01); *A61B 90/361* (2016.02); *A61B 2017/00477* (2013.01); *A61B 2034/305* (2016.02); *G05B 2219/45123* (2013.01); *G05B 2219/49305* (2013.01); *Y10S 901/02* (2013.01); *Y10S 901/41* (2013.01)

(58) Field of Classification Search
  CPC .... A61B 2017/00477; A61B 2034/305; G05B 2219/45123; G05B 2219/49305; G16H 40/40; Y10S 901/02; Y10S 901/41
  See application file for complete search history.

(56) References Cited

U.S. PATENT DOCUMENTS

| | | | |
|---|---|---|---|
| 5,850,573 A | 12/1998 | Wada | |
| 6,003,065 A * | 12/1999 | Yan | G06F 9/50 709/200 |
| 6,061,617 A | 5/2000 | Berger et al. | |
| 6,331,181 B1 | 12/2001 | Tierney et al. | |
| 6,520,727 B1 | 2/2003 | Babbs et al. | |
| 6,542,789 B2 | 4/2003 | Ufheil | |
| 6,594,552 B1 | 7/2003 | Nowlin et al. | |
| 6,645,196 B1 | 11/2003 | Nixon et al. | |
| 6,725,080 B2 | 4/2004 | Melkent et al. | |
| 6,837,883 B2 | 1/2005 | Moll et al. | |
| 6,866,671 B2 | 3/2005 | Tierney et al. | |
| 6,879,880 B2 | 4/2005 | Nowlin et al. | |
| 6,957,351 B2 | 10/2005 | Emberty et al. | |
| 7,006,895 B2 | 2/2006 | Green | |
| 7,076,536 B2 * | 7/2006 | Chiloyan | G06F 9/4411 709/220 |
| 7,083,571 B2 | 8/2006 | Wang et al. | |
| 7,087,049 B2 | 8/2006 | Nowlin et al. | |
| 7,107,090 B2 | 9/2006 | Salisbury et al. | |
| 7,107,124 B2 | 9/2006 | Green | |
| 7,155,315 B2 | 12/2006 | Niemeyer et al. | |
| 7,373,219 B2 | 5/2008 | Nowlin et al. | |
| 7,379,790 B2 * | 5/2008 | Toth | G16H 40/40 700/245 |
| 7,457,831 B2 | 11/2008 | Orleth et al. | |
| 7,983,793 B2 | 7/2011 | Toth et al. | |
| 8,634,957 B2 | 1/2014 | Toth et al. | |
| 9,345,546 B2 * | 5/2016 | Toth | G16H 40/40 |
| 2002/0032451 A1 | 3/2002 | Tierney et al. | |
| 2002/0077645 A1 | 6/2002 | Wiener et al. | |
| 2002/0083228 A1 * | 6/2002 | Chiloyan | G06F 9/4411 710/9 |
| 2002/0124046 A1 * | 9/2002 | Fischer | G06F 9/4415 709/201 |
| 2004/0088279 A1 | 5/2004 | Atzmueller et al. | |
| 2005/0251156 A1 * | 11/2005 | Toth | G16H 40/40 606/153 |
| 2007/0048863 A1 | 3/2007 | Rodgers et al. | |
| 2008/0154246 A1 | 6/2008 | Nowlin et al. | |
| 2014/0188131 A1 * | 7/2014 | Toth | G16H 40/40 606/130 |

FOREIGN PATENT DOCUMENTS

| | | |
|---|---|---|
| JP | S63106779 U | 7/1988 |
| JP | S6446183 U | 3/1989 |
| JP | H03208585 A | 9/1991 |
| JP | H06315881 A | 11/1994 |
| JP | H08263125 A | 10/1996 |
| JP | H08275958 A | 10/1996 |
| JP | 2001087281 A | 4/2001 |
| JP | 2001346808 A | 12/2001 |
| JP | 2002360602 A | 12/2002 |
| JP | 2004129782 A | 4/2004 |

OTHER PUBLICATIONS

Chinese Patent Application No. 201010536630.2 First Office Action dated Aug. 18, 2011, with English translation, 34 pages.
Kazanzides, Peter et al., "Force Sensing and Control for a Surgical Robot," Int. Conference on Robotics and Automation, May 1992, Nice, France; pp. 612-617, vol. 1, IEEE.
Office Action dated May 22, 2015 for Japanese Application No. 20140104966 filed May 21, 2014, 7 pages.
PCT/US05/14414 International Search Report and Written Opinion of the International Search Authority, dated Oct. 18, 2005, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

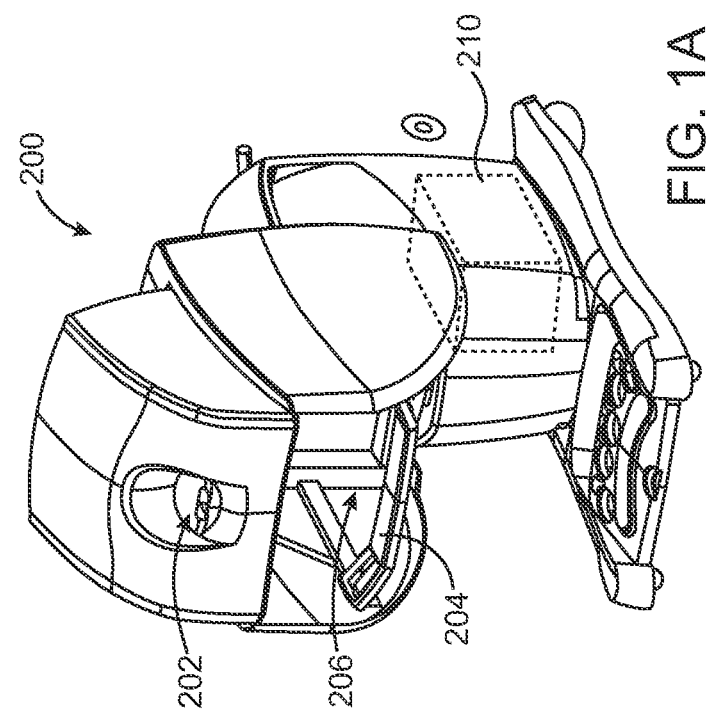
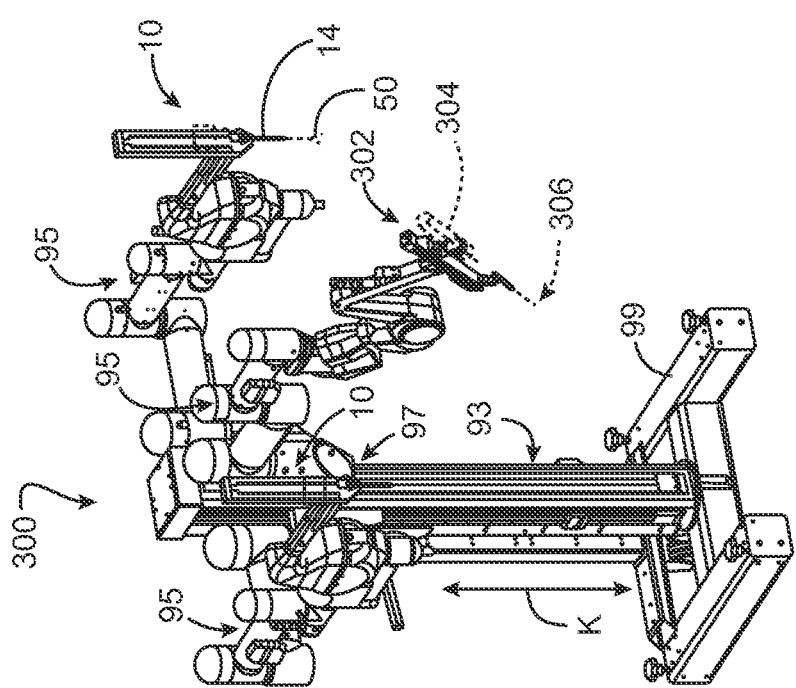

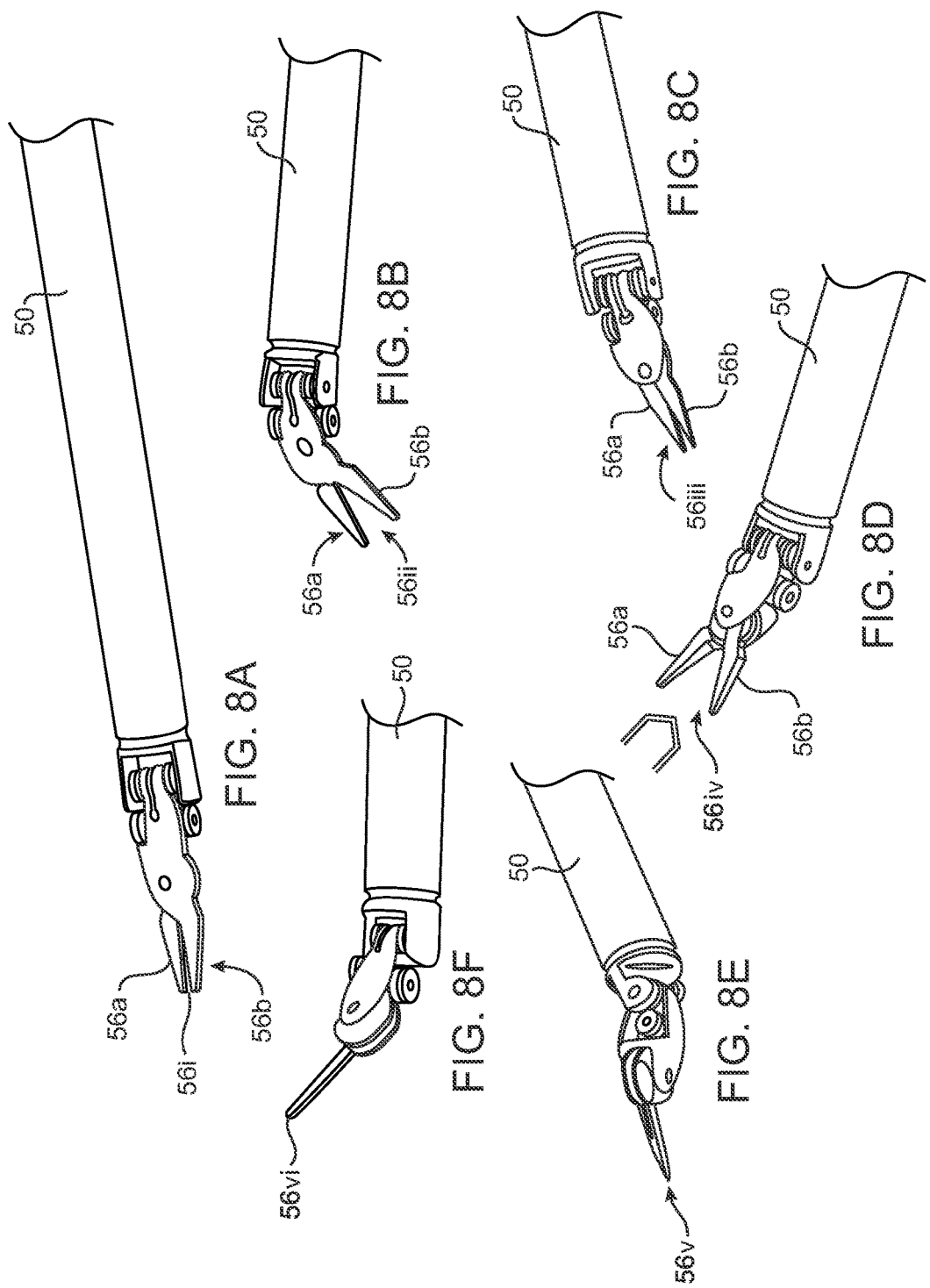

TOOL MEMORY-BASED SOFTWARE UPGRADES FOR ROBOTIC SURGERY

BACKGROUND OF THE INVENTION

The present invention is generally related to medical and/or robotic devices, systems, and methods. For example, the invention allows the system software of robotic systems used in surgery or other applications to be revised by including update data in a memory of a tool which can be mounted on a robotic arm. The software update may facilitate the use of tools which were not available when the robotic system software was installed. In another example, a medical device system having a disposable component and a reusable processor may have the processor software updated by use of a disposable instrument, thereby allowing the instrument to be used for both treating tissues and updating system programming.

Minimally invasive medical techniques are intended to reduce the amount of extraneous tissue that is damaged during diagnostic or surgical procedures, thereby reducing patient recovery time, discomfort, and deleterious side effects. While many of the surgeries performed each year in the US could potentially be performed in a minimally invasive manner, only a portion of current surgeries use these advantageous techniques due to limitations in minimally invasive surgical instruments and the additional surgical training involved in mastering them.

Minimally invasive telesurgical systems for use in surgery have been developed to increase a surgeon's dexterity and avoid some of the limitations on traditional minimally invasive techniques. In telesurgery, the surgeon uses some form of remote control (such as a servomechanism or the like) to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control the motion of servomechanically operated instruments The servomechanism used for telesurgery will often accept input from two master controllers (one for each of the surgeon's hands) and may include two or more robotic arms. It will often be advantageous to change the position of the image capturing device so as to enable the surgeon to view the surgical site from another position. Mapping of the hand movements to the image displayed from the image capture device can help the surgeon provide more direct control over movement of the surgical instruments.

While the new telesurgical systems and devices have proven highly effective and advantageous, still further improvements would be desirable. For example, a wider variety of surgical instruments may be adapted or developed for mounting to these new robotic arms for performing existing and new minimally invasive procedures. By having the flexibility of attaching a wide variety of new instruments having new surgical end effectors to existing telesurgical systems, surgeons may be able to perform more and more surgical procedures using minimally invasive techniques. The existing systems, including their software, processors, and manipulator actuation structures, are already being deployed in surgical rooms throughout the country and throughout the world. Unfortunately, as new robotic surgical instruments are developed, updating this base of existing capital equipment can be slow, expensive, and difficult to implement uniformly, particularly for the robotic surgical systems already located in other countries.

For the reasons outlined above, it would be advantageous to provide improved devices, systems, and methods for robotic surgery. It would also be advantageous to provide improvements for other robotic applications. Similarly, as medical instrument systems having both reusable capital equipment with reprogrammable processors and disposable components proliferate, it may be advantageous to provide improved devices, systems, and methods for updating the capital equipment, as well as providing business methods for commercializing systems for telesurgery, robotics, medical instruments, and a variety of other fields.

BRIEF SUMMARY OF THE INVENTION

The present invention generally provides improved robotic devices, systems, and methods for use in robotic surgery and other robotic applications. The present invention also provides improved medical instrument devices, systems, and methods for using these improved medical systems, particularly for medical systems including both a reprogrammable processor and a limited-use medical treatment probe. Business methods may also be provided by the present invention for commercializing capital equipment having related peripherals and limited-use components. In some embodiments, the invention may incorporate a memory into a limited-use component such as a robotic surgical tool. Machine readable code cant be stored in that tool memory with data and/or programming instructions to be implemented by the system processor. This can allow the programming of the system processor to be effectively updated by shipping of new surgical robotic tools or other disposables. Optionally, once the update data or programming instructions have been downloaded by the processor from a tool, subsequent tools can take advantage of the updated processor programming without requiring repeated downloading of the new software. This can avoid delays and expense, for example, when surgical instruments are repeatedly removed and attached to a robotic arm during one or more surgical procedures.

In a first aspect, the invention provides a robotic system comprising a robotic arm having a tool holder and a signal interface. A plurality of robotic tools are each receivable by the holder for manipulation by the robotic arm. A processor has a memory and is coupled to the robotic arm. The processor memory comprises robotic tool data associated with the plurality of tools. The processor directs movement of a robotic tool received by the tool holder using associated tool data from the processor memory. A first additional tool has a memory with additional tool data or code. The memory of the processor may lack this additional tool data or code prior to coupling of the first additional tool to the robotic arm. The first tool transmits the additional tool data or code to the processor via the tool signal interface. The processor stores the additional data or code in the processor memory for use in directing movement of the robotic arm after the first additional tool is removed from the tool holder. The additional data or code may also be used while the first additional tool is still mounted to the arm.

In the exemplary embodiments, the tools comprise surgical robotic tools having a plurality of differing surgical end effectors, so that the robotic system comprises a surgical robotic system.

The first additional tool may have a tool type identifier. A second additional tool may also have the same tool type identifier. The processor may store the additional tool data from the first additional tool in the memory, and may, in response to the tool type identifier of the second additional tool, direct movement to the robotic arm using the additional tool data from the processor memory when the second additional tool is received by the tool holder. By making use of the additional tool data from the memory rather than downloading this new data each time a new tool is attached the system may avoid system delays during tool changes.

The processor may store the additional tool data in an update list of the processor memory. The update list may comprise data associated with a plurality of additional tools of differing types. The processor memory may also comprise a native list of data associated with the plurality of tools.

The processor may give priority to the additional tool data of the update list over the tool data of the native list when similar tool identifiers are included on both so as to allow effective revisions to the tool data of known tools. The memory may also include a reject tool list, with the processor inhibiting use of an additional tool having a rejected tool identifier included on the reject tool list.

The processor may comprise machine readable code for directing movement of the tools. The machine readable code may embody a software capability identifier, often in the form of a software revision identifier, and the additional tool data may specify a minimum software capability and/or revision. The processor may inhibit use of the first additional tool if the software revision is older than the minimum software revision. This allows, for example, a distributor of the tools to specify a minimum processor software capability if a new tool is to be used, for example, so that a tool requiring a particular subroutine will only be used on systems having processors that include that subroutine.

A second tool may include machine readable code embodying tool data, including tool-movement directing data and a maximum software revision. The processor may direct movement of the second tool using tool data from the memory of the processor when the software revision identifier of the processor is older than the maximum specified software revision of the second tool. This allows the processor to selectively make use of resident tool data in a memory of the processor rather than taking time to download that same information from an additional tool which has been sitting for several months or years, long after the processor software has already been updated, and possibly after the data in the tool memory has been updated.

At least some of the plurality of tools may comprise legacy tools lacking some or all of the additional tool data. The additional tool data may include an indicator or flag so as to alert the processor that it should make use of the additional tool data. This indicator or flag may be turned off or negated in the legacy tools.

Optionally, an input device may be coupled to the processor for receiving input movements, with the processor effecting an output movement of a tool received by the tool holder corresponding to the input movement so that the robotic system comprises a master-slave robotic system. A first configuration time may correspond to configuring the processor for directing movement using the tool data from the memory, and a second configuration time may correspond to configuring the processor for directing movement using additional tool data downloaded from the mounted tool. The second configuration time may be longer than the first configuration time. The processor may be adapted to limit cumulative configuration time by storing the additional tool data from the first tool in the memory, and using that stored additional data for the first additional tool (after removal and attachment), a second additional tool, and/or the like.

In another aspect, the invention provides a medical instrument system comprising a plurality of medical instruments. Each instrument has a tissue treatment delivery surface and an interface. A processor has an interface sequentially couplable with the instrument interfaces. The processor has a memory storing code or data, and controls treatment delivered by the tissue treatment delivery surfaces of the instruments using the stored code or data. A first additional instrument has a tissue treatment delivery surface, an instrument memory, and an interface coupled to the instrument memory so as to provide communication between the instrument memory and the processor when the additional instrument interface is coupled to the processor interface. The processor is configured to store update code or data from the instrument memory in the memory of the processor. A second additional tool has a tissue treatment delivery surface and an interface. The processor controls treatment delivered by the tissue treatment delivery surface of the second additional tool using the update code or data communicated from the instrument memory of the first additional instrument.

In many embodiments, the plurality of medical instruments will comprise a plurality of medical instrument types. Each medical instrument may have an instrument memory coupled to the interface. The memory may comprise a type identifier, each instrument type having associated instrument type data embodied by the machine readable code. The processor may direct treatment via the tissue treatment surface of an instrument coupled with the processor using associated instrument data in response to the type identifier of the coupled instrument. The second additional instrument may have the same type identifier as the first additional instrument.

In another aspect, the invention provides a robotic method comprising sequentially mounting a plurality of robotic tools of different types to a robotic arm. Movement of each sequentially mounted robotic tool is directed with a processor using data or code associated with the mounted robotic tool type. The data or code for the plurality of tools is stored in the memory of the processor. A first additional robotic tool is mounted to the robotic arm. Update tool data or code is transmitted from a memory of the first tool to the processor. Movement of the robotic arm is directed by the processor using the update tool data or code.

The tools may comprise surgical robotic tools having a plurality of different surgical end effectors. The movement of the surgical end effectors may be directed by a surgeon moving an input device so as to perform a surgical procedure. Hence, the robotic arm and input device may be components of a master-slave surgical robotic system.

There will often be a configuration time or a download delay involved when the processor downloads the additional tool data from a mounted tool. This configuration time may be substantially greater than the time involved in configuring the processor for directing movement of a tool when the desired data is already resident in a memory of the processor. To limit the overall reconfiguration time and avoid delays during tool changes, the processor may store the additional tool data downloaded from a mounted tool for use with other tools of a similar type. The additional tool data may be stored in an update list of the memory, while the tool data associated with the known tool types may be stored in a native list of the memory of the processor. When a tool identifier is listed in both the native memory (so that the tool was known when the processor software revision was loaded into the processor, for example) but the tool data is later updated (for example, to lower a grip strength limit to increase safety margins based on experience when using the tool in the field) the same tool type may be included in both lists. Under such circumstances, it may be advantageous to give priority to the update list, for example, by checking the update list first, and if a tool identifier is found therein, making use of that information and not going on to check the native list. This allows tool data to be effectively updated by distributing appropriate additional tools having revised tool data. Additional options include a reject list in the processor memory, with the processor inhibiting use of a tool having a tool identifier included on the reject tool list.

The invention can facilitate the distribution of tools which are intended for use with existing robotic systems and other capital equipment, but which tools have been developed after the systems have been installed in the field. However, not all previously installed systems may have the capability of utilizing newly-developed tools. For example, an installed robotic surgery system may have software that is not configured to accommodate a sliding joint at the distal end effector. If a new tool is developed which makes use of such a sliding joint, it may be easier to update the software of an installed robotic surgery system using magnetic or optical recording media, a network, or other conventional means, rather than taking the time to download an extensive software revision via a surgical robotic tool coupled to a robotic surgery system in the middle of a surgical procedure. Similarly, if a new tool is developed which requires hardware that is not installed on some robotic systems, such as an ultrasound driver for an ultrasound tool. Advantageously, the processor memory may store system capability data, and the additional tool data may identify a minimum system capability. The processor can inhibit use of the first additional tool if the system capability data is incompatible with the minimum system capability of the first additional tool. For example, the processor in the memory may store a software revision identifier and the additional tool data may include a minimum software revision.

After a tool has been distributed to systems in the field for an extended period of time, software revisions may be implemented on the installed systems for a variety of reasons. If the programming of the processor is to be updated, it will often be advantageous to avoid any time delay involved in downloading tool data to the processor memory by including the additional tool data with a system software revision. The memory of the processor may store a software revision identifier, and a second tool may have a tool memory with tool data including a maximum software revision. Although the tool memory may also include data for use in directing movement to the tool, the processor may direct movement of the second tool using tool data from the processor memory in response to the software revision identifier of the processor being older than the maximum software revision of the second tool. This may avoid, for example, the use of obsolete tool data stored on a memory of an old tool.

At least some of the plurality of the tools may comprise legacy tools. Such legacy tools need not necessarily include a tool memory with tool data sufficient for using the tool if the tool is not known to the robotic system. Nonetheless, a tool type identifier may be transmitted from each legacy tool mounted on the arm to the processor. The processor may identify the tool data in the processor memory using the transmitted tool type identifier. Optionally, the processor may differentiate between legacy tools and tools having full downloadable additional tool data based on data transmitted from the tool. Ideally, systems sold after legacy tools will still be compatible with the earlier-distributed legacy tools, while many newly-distributed tools having downloadable tool data will still be compatible with older systems, even if the older systems cannot fully take advantage of the downloadable data.

In another aspect, the invention provides a method comprising mounting a first robotic tool to a robotic arm. Movement of the mounted first tool is directed with a processor using first tool data. The first tool data is stored in a memory of the processor prior to mounting the first tool. A second robotic tool is mounted to the robotic arm. The second robotic tool has a memory with data associated with the second robotic tool. The second tool data is transmitted from the second tool to the processor. Movement of the mounted second tool is directed with the processor using the transmitted second tool data.

The second tool data need not be stored in the memory of the processor prior to mounting the second tool. A third robotic tool may be mounted to the robotic arm. The third robotic tool may have a tool identifier corresponding to a tool identifier of the second tool. Movement of the third tool may be directed by the processor using the transmitted second tool data. This can avoid repeated delays that might be imposed by downloading similar tool data from tools of the same type into the processor.

The third tool may be mounted to the robotic arm prior to mounting the second tool. Movement of the third tool may be directed using third tool data prior to mounting of the second tool. The second tool data may supercede the third tool data for tools having the same tool type identifier as the second tool after the second tool is mounted.

In another aspect, the invention provides a medical instrument system revision method comprising sequentially coupling a plurality of medical instruments to a processor, each instrument having a tissue treatment delivery surface and an interface. Treatment delivery by the tissue treatment delivery surfaces of the sequentially coupled instruments may be controlled using data stored in a memory of the processor. A first additional instrument may be coupled to the processor. The first additional instrument may have a tissue treatment delivery surface and an instrument memory. Update data may be transmitted from the memory of the additional instrument to the processor. The transmitted update data may be stored in the memory of the processor, and treatment delivery from a tissue treatment delivery surface of a second additional tool may be controlled using the stored update data.

The update data may optionally define a machine readable code embodying program instructions for implementing method steps for treating tissue using the tissue treatment delivery surface of a tool. Optionally, the update data may comprise data representing physical parameters of a treatment tool type. For example, when used with a surgical robotic system, the update data may represent geometric joint locations, tool strength limits, offsets, and the like.

The additional instrument may be decoupled from the processor and later recoupled back with the processor. The treatment delivery may be controlled with the recoupled additional instrument using the stored update data so as to avoid repeated downloading of the update data from the memory of the additional instrument.

In another aspect, the invention provides a method comprising providing a plurality of systems. Each system has a processor, and the systems are provided to a plurality of customers. A plurality of peripheral or limited-use devices are distributed to the customers. Each device can be coupled to a system so as to perform a primary function. Programming code or data of the processors are updated using memories of the coupled devices so as to alter the performance of the primary function after the devices are decoupled from the systems.

BRIEF DESCRIPTION OF THE DRAWINGS

FIGS. 1A and 1B are perspective views illustrating a master surgeon console for inputting a surgical procedure and a robotic patient-side cart for robotically moving surgical instruments at a surgical site, respectively.

FIGS. 8A-8F are perspective views of a variety of different end effectors for tools of different types.

DETAILED DESCRIPTION OF THE INVENTION

Figure 2:
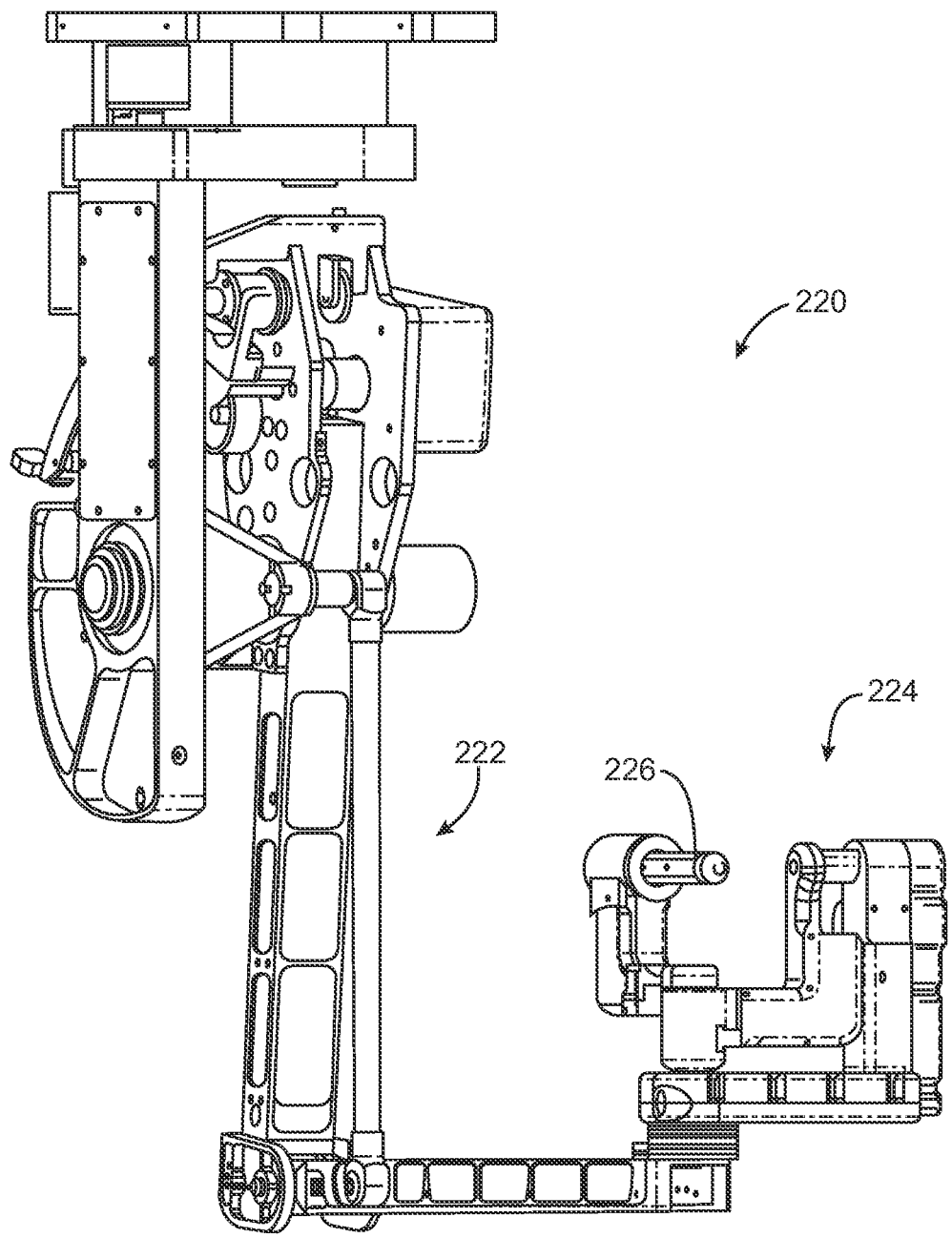
FIG. 2 is a side view showing an exemplary input device for use with the master control station of FIG. 1A.

The present invention generally provides robotic and/or medical instrument systems, devices, and methods. The invention is particularly useful for updating reconfigurable control systems for robotic and medical instrument processors, often allowing upgrades to be implemented in systems having processors that were programmed for use with a variety of instruments or tools. By including a memory with a new instrument or tool, and by including a data interface in the coupling arrangement between the instrument or tool and the system processor, the instrument or tools may be used as a software update distribution mechanism. This allows a system manufacturer to increase the software capabilities of robotic or medical instrument systems sold to customers throughout the US and/or throughout the world, without requiring that support personnel personally visit the installed instruments, and without having to rely entirely on telecommunications links such as the Internet.

While the most immediate application for the present invention may include robotic surgical systems, the inventions described herein may also find applications in other robotic systems. Along with master-slave telerobotic systems, the invention may find applications in more conventional autonomous industrial robots and the like. The invention may also find advantageous applications for use in other medical instrument systems, particularly those having both reprogrammable processors and disposable or other limited-use treatment probes. The invention may find applications in computing and telecommunication systems to allow programming to be updated using peripheral or disposable elements having some other primary purpose, including updating of the software of a printer or computer using a memory of an ink-jet (or other) printing cartridge, or the like.

A tool or instrument used to reprogram the system software is sometimes referred to as an "update" tool or instrument, an "additional" tool or instrument, and/or a "new" tool or instrument. As used herein, the term "tool" encompasses robotic tools that have robotic end effectors for coupling to robotic systems. The term "instrument" encompasses medical instruments including those having medical treatment surfaces (such as surgical end effectors in the form of graspers, scalpels, electrosurgical probes, ultrasound probes, and the like). In the exemplary embodiment, a robotic surgical system makes use of any of a series of removable and replaceable end effectors supported by a robotic arm, so that the end effector assembly is both a tool and an instrument. In robotic embodiments used in non-surgical applications, the end effector assembly may comprise a robotic tool that is not a medical instrument. Similarly, in non-robotic medical instrument embodiments, the instrument assembly having the treatment surface need not be an articulable robotic tool. Nonetheless, those skilled in the art should understand that non-medical robotic systems and non-robotic medical instrument systems may include many of the components, programming, and interactions described herein.

The data, reprogrammable software, program method steps, and method steps described herein may be embodied in a machine readable code and stored as a tangible medium in a wide variety of differing configurations, including random access memory, non-volatile memory, write once memory, magnetic recording media, optical recording media, and the like. Hence, the term "code" can encompass both programming instructions and data. Along with software, at least some of the programming and data may be embodied in the form of hardware or firmware. The term "additional data" encompasses revised, corrected, or different parameters or other information, as well as new parameters and the like.

Referring to FIG. 1A of the drawings, an operator workstation or surgeon's console of a minimally invasive telesurgical system is generally indicated by reference numeral 200. The workstation 200 includes a viewer 202 where an image of a surgical site is displayed in use. A support tool 4 is provided on which an operator, typically a surgeon, can rest his or her forearms while gripping two master controls (see FIG. 2), one in each hand. The master controls or input devices are positioned in a space 206 inwardly beyond the support 204. When using the control workstation 200, the surgeon typically sits in a chair in front of the control station, positions his or her eyes in front of the viewer 202 and grips the master controls, one in each hand, while resting his or her forearms on the support 204.

In FIG. 1B of the drawings, a cart or surgical station of the telesurgical system is generally indicated by reference numeral 300. In use, the cart 300 is positioned close to a patient for which surgery is planned, and the base of the cart is then maintained at a stationary position until a surgical procedure has been completed. Cart 300 typically has wheels or castors to render it mobile. The workstation 200 is typically positioned at some distance from the cart 300, optionally being separated by a few feet within an operating room, although cart 300 and workstation 200 may alternatively be separated by a significant distance.

The cart 300 typically carries three robotic arm assemblies. One of the robotic arm assemblies, indicated by reference numeral 302, is arranged to hold an image capturing device 304, e.g., an endoscope, or the like. Each of the two other arm assemblies 10 includes a surgical instrument 14. The endoscope 304 has a viewing end 306 at a distal end of an elongate shaft. Endoscope 304 has an elongate shaft to permit viewing end 306 to be inserted through an entry port into an internal surgical site of a patient's body. The endoscope 304 is operatively connected to the viewer 202 to display an image captured at its viewing end 306 on the viewer. Each robotic arm assembly 10 is normally operatively connected to one of the master controls. Thus, the movement of the robotic arm assemblies 10 is controlled by manipulation of the master controls. The instruments 14 of the robotic arm assemblies 10 have end effectors mounted on wrist members, which are in turn pivotally mounted on distal ends of elongate shafts of the instruments 14. Instruments 14 have elongate shafts to permit the end effectors to also be inserted through entry ports into the internal surgical site of a patient's body. Movement of the end effectors relative to the ends of the shafts of the instruments 14 is also controlled by the master controls.

The robotic arms 10, 302 are mounted on a carriage 97 by means of setup joint linkages 95. The carriage 97 can be adjusted selectively to vary its height relative to a base 99 of the cart 300, as indicated by arrows K. The setup joint linkages 95 are arranged to enable the lateral positions and orientations of the arms 10, 302 to be varied relative to a vertically extending column 93 of cart 300. Accordingly, the positions, orientations and heights of the arms 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position. Workstation 200 and cart 300 are described in more detail in U.S. Pat. No. 6,424,885, the full disclosure of which is incorporated herein by reference.

Figure 3:
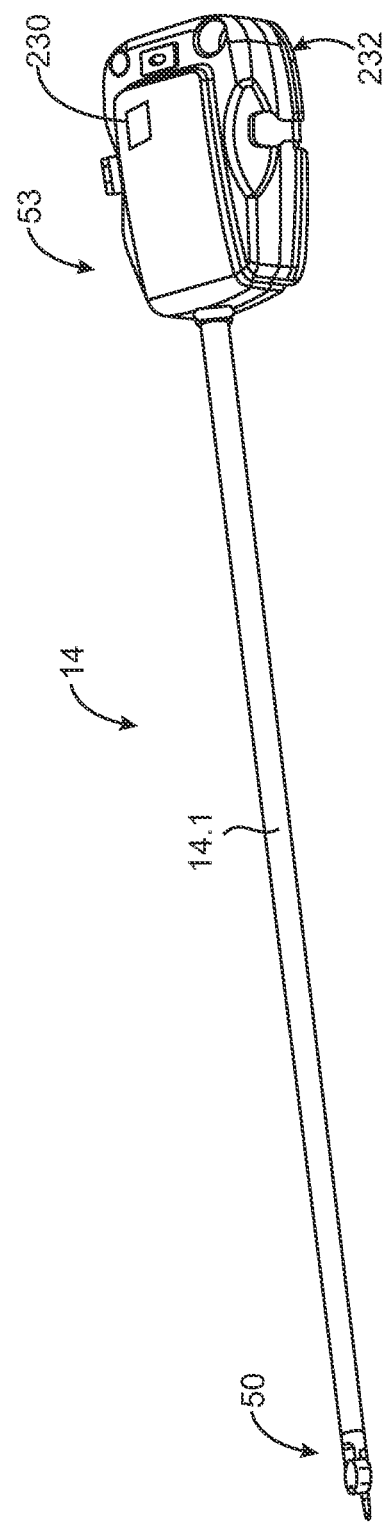
FIG. 3 is a perspective view of an exemplary robotic surgical instrument or tool having a memory and a data interface.

An exemplary input device 220 and surgical instrument 14 are illustrated in FIGS. 2 and 3, respectively. Input device 220 includes an arm 222 and a wrist 224 which allow positional and orientational movement of an input handle 226 relative to the structure of workstation 200 (see FIG. 1A). Handle 226 will generally move with a plurality of degrees of freedom relative to the workstation structure, the exemplary input device 220 providing six degrees of freedom for movement of handle 226. The linkage supporting the handle may include more or less than six degrees of freedom.

Referring now to FIG. 3, surgical instrument 14 generally includes a surgical end effector 50 supported relative to a housing 53 by an elongate shaft 14.1. End effector 50 may be supported relative to the shaft by a distal joint or wrist so as to facilitate orienting the end effector within an internal surgical workspace. Proximal housing 53 will typically be adapted to be supported by a holder of a robotic arm.

As described in more detail in U.S. Pat. No. 6,331,181, the full disclosure of which is incorporated herein by reference, instrument 14 will often include a memory 230, with the memory typically being electrically coupled to a data interface of a holder engaging surface 232 of housing 53. This allows data communication between memory 232 and a robotic surgical processor of workstation 200. More specifically, as can be understood by reference to FIGS. 1A through 4. Workstation 200 shown in FIG. 1A will typically include a processor 210. Processor 210 effects corresponding movement of a surgical movement 14 mounted to robotic arm 10 in response to movement of an input handle 226.

Figure 4:
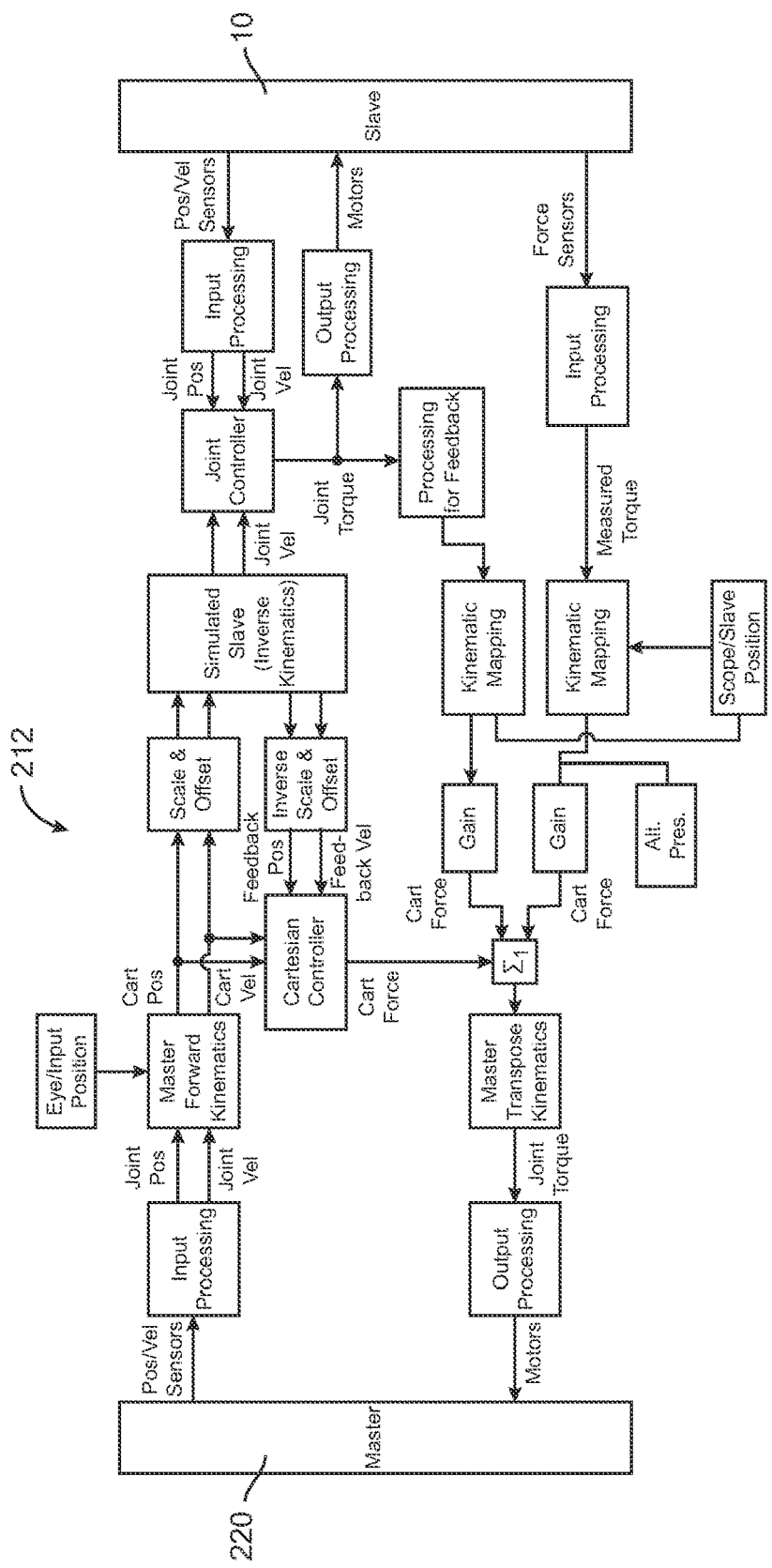
FIG. 4 shows a block diagram representing control steps followed by the control system of a minimally invasive surgical robotic apparatus in effecting movement of the end effector of the tool of FIG. 3 in response to movement of the input device of FIG. 2.

In the exemplary embodiment, processor 210 comprises software embodying a control logic 212 (illustrated schematically in FIG. 4). This control logic effects movement of an end effector 50 within an internal surgical site by pivoting an instrument shaft 14.1 about a minimally invasive insertion point. The control logic 212 employed by processor 210 generates motor drive signals in response to an input handle movement. These motor drive signals are transmitted to the robot arms, and cause to effect movement at the end effector that correspond to movement at the input handle, as is described in more detail in the '885 patent, previously incorporated herein by reference. As can be understood by reference to the diagram of the control logic illustrated in FIG. 4, the joint kinematics of both the robotic arm 10 and the surgical instrument 14 are simulated within the controller.

A wide variety of robotic surgery instrument types are described in the patent literature. These different robotic too types are often removed and replaced during a robotic procedure, so as to allow the surgeon to perform differing functions. For example, a scissor structure may be removed and replaced with an electrosurgical scalpel. Such different tool types may have wrists or other tool joints with different geometries, such as differing separation distances between joint axes. Different tool types may also have differing ranges of motions about each axis, different joint binding positions or singularities, and/or other differences in their joint geometries, as can be understood with reference to FIGS. 8A-8F. Additionally, two different surgical instrument end effector structures will often have differing strengths, different inertias, different effective gearing ratios between motion about their axes and movement of associated driving elements, and the like. Still further differences between different tool types may include the presence or absence of an electrosurgical capability, the useful life of a tool, the ability to replace end effector elements, or the like. Logic 212 of processor 210 can accommodate these differing tool kinematics and properties when information regarding the tool type currently mounted to a robotic arm 10 is made available to the processor.

Figures 5, 6A, 6B:
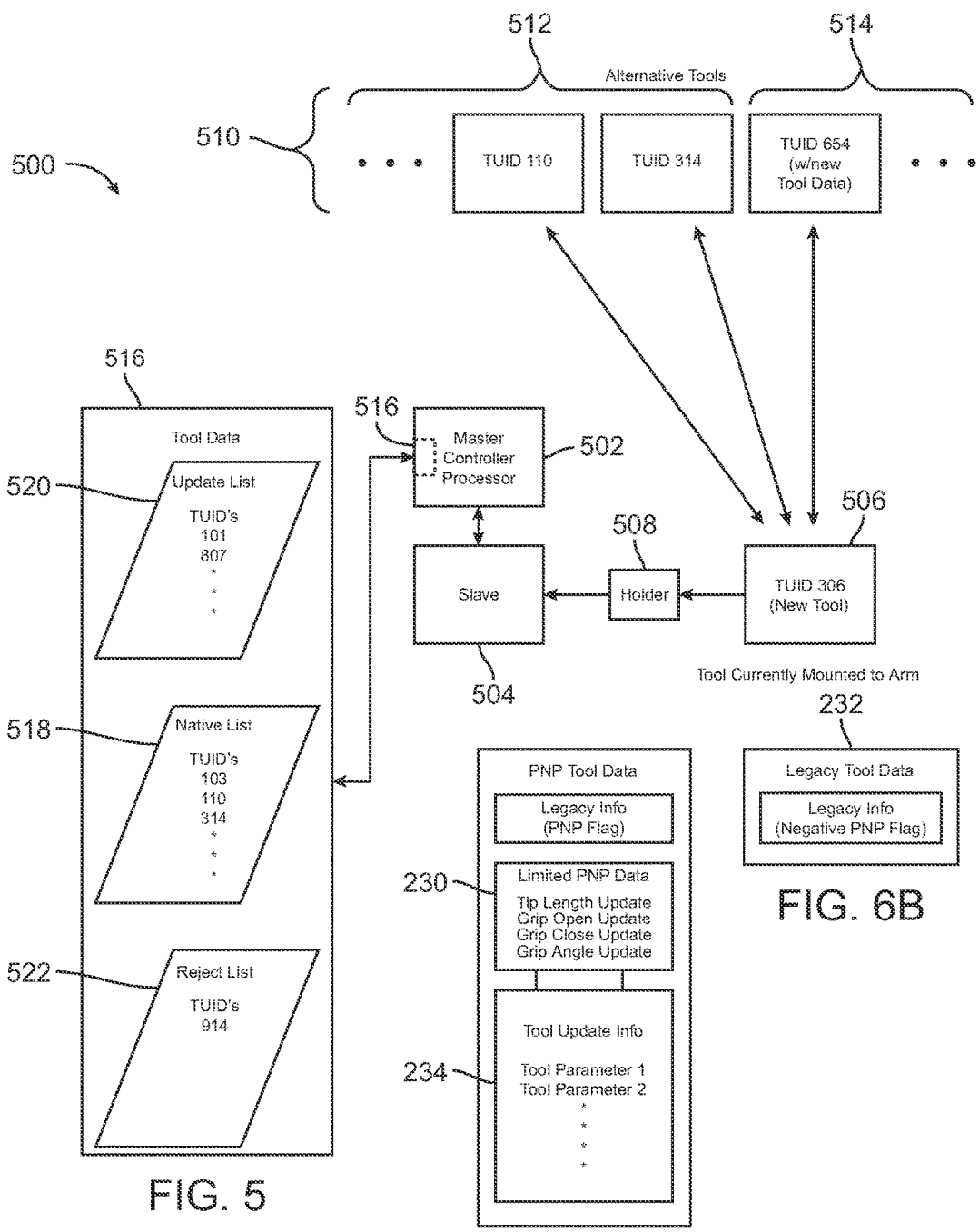
FIG. 5 is a functional block diagram schematically illustrating components of a robotic surgical system according to the principles of the present invention.
FIGS. 6A and 6B schematically illustrate additional or "new" tool data, and legacy tool data, respectively, as stored in memories of robotic surgical tools for use in the system of FIG. 5.

Referring now to FIG. 5, a robotic surgical system 500 is schematically illustrated as including a master controller 502 coupled to a slave robotic arm 504 so as to move a robotic tool 506. Tool 506 is held by a tool holder 508 of robotic arm 504. A plurality of alternative tools 510 are available to sequentially replace tool 506 by detaching tool 506 from the holder 508, and instead engaging a selected tool from among the plurality of tools on the robot arm. To allow the logic of controller processor 508 to adjust for the tool currently coupled to the slave 504 the holder 508, data from the mounted tool is transmitted via the holder to the slave and on to the processor 502. The transmitted tool data typically includes a tool type identifier.

The plurality of tools 510 may include two different groupings of tool types: "known" or "legacy" tools 512 and "new" or "additional" tools 514. Known tools 512 may include tool types which were developed and known when master controller processor 502 was programmed, when the last software revision downloaded to processor 502 was written, or the like. Known tools 512 include tools that have tool type identifiers (sometimes referred to as Tool Unique Identifiers (TUID)) which are included in a memory 516 of processor 502. In some embodiments, it may be desirable to distribute concurrently both plug-and-play or system updating tools and non-plug-and-play tools. This may decrease average tool costs while still allowing many of the capabilities described herein.

Advantageously, when a known tool (such as tool type 110) is mounted to slave robotic arm 504, transmission of the tool type identifier (TUID 110) to the master controller 502 via tool holder 508 provides sufficient information for the master controller processor to reconfigure its software to properly control movement of the slave, instrument, and end effector. More specifically, the tool type identifier is sufficient for processor 502 to look up the tool kinematic data from the native list 518 of processor memory 516. This can be done quite quickly, without delaying use of the robotic tool by the surgeon.

In contrast, new tools 514 may include end effectors, driving systems, tool strengths, or other tool characteristics that have been developed or revised since the programming of processor 502. To allow such a new tool type (such as tool TUID 306) to be controlled by processor 502, the processor may determine from the tool type identifier that the desired tool kinematic data is not available in the memory 516 of the processor. The processor may then download the desired tool kinematic information via holder 508 (or some alternative data interface) and store this new information in an update list 520 of the processor memory 516. This effectively allows the processor to be reprogrammed to accommodate the new tool.

The information included in tool memory 230 of a new tool type is schematically illustrated in FIG. 6A. Legacy tool data 232 resident in a memory of a known tool is schematically illustrated in FIG. 6B. As used herein, the term "plug-and-play" and the initials "PNP" encompass the capability of a robotic or medical instrument and/or system to update the system programming from a memory of a tool or instrument.

In the exemplary embodiment, legacy tool data 232 may be embodied in memory 230 of instrument 14 (see FIGS. 3 and 6B), with the exemplary memory comprising Dallas part DS 2505. Circuitry coupling the memory of the instrument to the instrument interface, and details regarding the instrument interface, can be found in U.S. Pat. No. 6,331,181. Alternative instruments, circuitry, and interfaces are also known, including those employed by the Zeus™ robotic surgical system previously commercialized by COMPUTER MOTION, Inc. of Santa Barbara, Calif.

The exemplary legacy tool data includes legacy information with a tool identifier that can be used to identify that particular tool, along with tool type identifier data. A unique Dallas chip number may be used as the tool identifier, and the tool identifier allows tracking of the use of that particular tool over its lifetime throughout numerous different surgical procedures on a plurality of different robotic arms and/or robotic systems. Some portion of the legacy information that is consistent throughout all the legacy tools may be used as a "negative PNP flag" so that robotic system 500 can determine that the legacy tool does not include additional tool data.

Referring now to FIG. 6A, additional or PNP tool data 230 includes legacy information analogous to that of legacy data 232 in FIG. 6B. This facilitates reverse compatibility and use of a new tool with systems 500 that do not have plug-and-play capability. However, the legacy information of new tool data 230 will include a PNP flag. This allows a system having plug-and-play capability to identify that the new tool includes the additional tool information and to make use of that information.

Along with legacy information, new tool data 230 will generally include tool update information 234 with a listing of tool parameters sufficient for system 500 to safely and effectively direct movement of the new tool in the surgical procedure. Several tool parameters may be listed, often comprising more than 10 parameters, and optionally comprising more than 100 or even more than 1000 parameters. In exemplary embodiments, new tool data 230 may comprise 2K, 8K, or 64K of data or more, exemplary memories on which the additional tool data 230 is stored comprising DALLAS SEMICONDUCTOR part numbers DS2505, DS2505V, or DS2505P.

In addition to both legacy information and tool update information 234, new tool data may include limited PNP info so as to allow a limited plug-and-play capability for older robotic surgical systems. In this exemplary embodiment, as will be described with reference to FIG. 8 below, the information may include a limited number of parameters, with each parameter corresponding to an associated tool parameter included in the full new tool data so that these tool parameters are repeated in the tool memory. An older robotic surgical system may download any parameter listed in the limited PNP data from the tool to the memory 516 of processor 500, optionally for use only with the mounted tool.

Referring now to FIG. 5, memory 516 of processor 502 may store the tool data in a variety of alternative tangible media, including magnetic recording media, optical recording media, RAM, ROM, and the like. In the exemplary embodiment, tool data may be stored, at least in part, in NVRAM (for the update list) and in a flash memory (for the native and reject lists). Tool data may also be stored at least in part in a random access memory of the master controller processor 502 during use. While a tool is mounted it may be beneficial to avoid altering the system behavior for that tool, even if an update tool of the same tool type is mounted to a different arm of the system. Once a mounted tool is removed and re-mounted, the system may take advantage of new data. Use of tool kinematic and strength information is more fully described in U.S. Pat. No. 6,424,885, previously incorporated herein by reference.

As used herein, tool data is stored in a "memory" of processor 502 when it is embodied in tangible media of system 500 which remains coupled to the system processor when a mounted tool is removed and replaced by any of the plurality 510 of alternative tools. Hence, data which is downloaded from the tool and recorded on magnetic or optical recording media, embodied in an EEPROM, or temporarily stored in a RAM of processor 502 or any other peripheral storage device of processor 502 is considered stored in a memory of the processor.

Processor 502 will typically comprise software and/or hardware capable of implementing program steps embodied in machine readable code so as to effect the methods of the present invention. In the exemplary embodiment, processor 502 comprises a processor 210 of controller workstation 200 (see FIG. 1A), ideally comprising a board having a plurality of commercially available processors, including Sham processors available from ANALOG DEVICES, Power PC processors available from MOTOROLLA, as well as memory and the like. The exemplary programming code is primarily written in "C" programming language, but a wide variety of other languages could also be used. Processor 502 may also comprise software and/or hardware distributed throughout the robotic surgical system, with arms 10, cart 300, and even holder 508 [see FIGS. 5 and 1B] often having local processing capability in any of a wide variety of distributed processing arrangements. Alternative processor architectures which may be adapted to make use of the methods and devices of the invention include those of the Zeus™ robotic surgery system previously commercialized by COMPUTER MOTION, INC.

Figure 7:
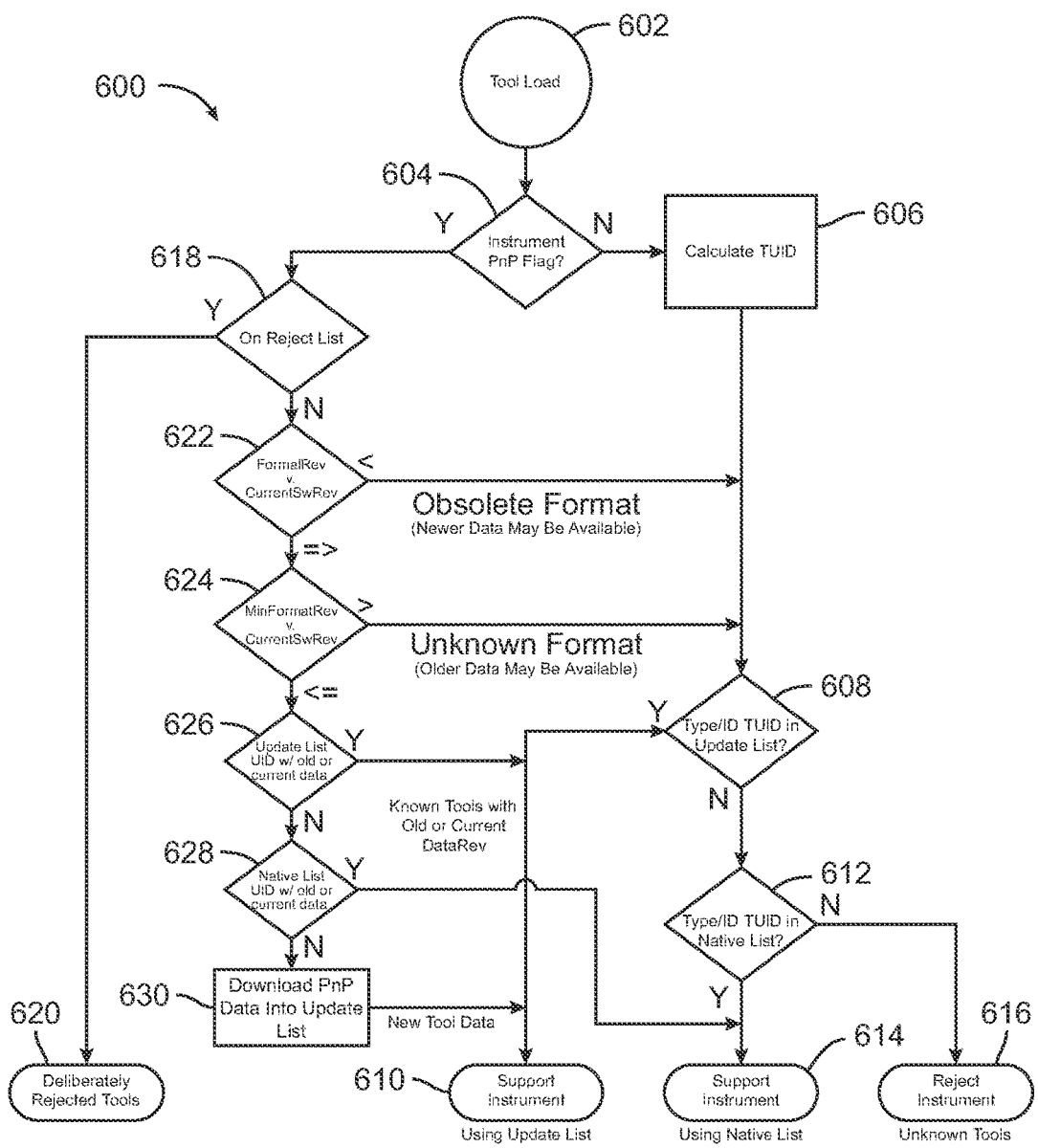
FIG. 7 is a flow chart illustrating program software embodying a method for using the system of FIG. 5, in which tools or surgical instruments can be used to update the software of a robotic surgical system.

Referring now to FIG. 7, a method 600 embodying the present invention starts when a tool is loaded 602 or mounted onto a robotic arm of the robotic system. Legacy information is downloaded from the memory of the tool, allowing the system to determine whether the tool memory has updated tool information 604. The data initially downloaded from the tool may include more than just the legacy data. In fact, if only legacy information is available the remainder of the initially downloaded information may be blank, which may be used as an indicator that the tool is a legacy tool. Downloading of this initial information from the tool to the processor of the system may be performed during mechanical engagement confirmation movements of the tool through the tool holder or interface, and thereby does not necessarily delay a surgical procedure. The downloaded legacy information will be sufficient to also allow the system to identify the tool type 606. In the exemplary system, the tool type identifier is calculated from one or more legacy fields in the legacy data. Alternative systems may simply read the tool type identifier from the tool memory.

First assuming that the mounted tool is a legacy tool which does not include the additional tool data, after the processor calculates the tool type identifier 606 the processor determines whether the tool is of a type that has previously been updated 608 (for example, by previously loading a plug-and-play tool of the same type as that which has been mounted onto the robotic arm). The processor may determine whether the tool type data has already been updated by comparing the tool type to update list 520 in the memory 516 of processor 502 (see FIG. 5). If the tool type is indeed included in the update list, processor 502 may control movement of the robotic arm and mounted tool using data already resident in the processor memory 516, thereby supporting the mounted instrument 610 without delaying for downloading of additional tool data. Supporting of the instrument may comprise, for example, reconfiguring software of the processor using the parametric tool data from memory 516 for the tool type identifier of the tool.

If the tool type is not listed in the update list, processor 502 may then determine if the tool type identifier is already included in the native list 518 of the processor memory 516 at step 612. If the tool identifier is included in native list 518, the processor can again support the mounted instrument 614 without downloading the additional data from the tool. Specifically, processor 502 is reconfigured using native list tool parametric information that is again already present in tool memory 516 when the tool is mounted to the robotic arm. Hence, once again downloading delays can be avoided.

Processor 502 effectively gives priority to the update list over the native list, so that tool parametric information may be effectively revised by distributing tools of an existing tool type (having a tool identifier of a known tool). For example, if a known tool type is found to perform more reliably if a prior strength of an infector torque is reduced, this allows updating of how these existing tools are used in the field. Optionally, the manufacturer may elect not to update tool types of previously-sold tools so as to avoid having a single tool (or two tools at the same time) react differently before and after an update or plug-and-play tool is used on a system. As we have assumed above that the mounted tool is not plug-and-play capable at step 604, if the desired tool parametric information for supporting the instrument is not available in processor memory 516 (in neither the native list 518 nor the update list 520), the system may reject the mounted instrument 616 so as to avoid attempting control movement of the tool without sufficient tool data. Note that along the path of the flow chart that assumes that the instrument is not plug-and-play capable, processor 502 first checks for the tool information on the update list before checking for the tool identifier on the native list 518.

The preceding discussion assumed that the mounted tool was not plug-and-play capable at step 604, that is, that the mounted tool was a legacy tool. If we instead assume that the tool mounted 602 on a robotic arm has additional tool data that may be used to update a system processor, the system processor may determine from the legacy data downloaded from the tool that the tool has plug-and-play capabilities at step 604. Despite the presence of this additional tool information in a memory in the tool, it may be advantageous to avoid downloading some or all of the additional tool data so as to limit delays during the tool swap. In method 600, the processor determines whether the mounted plug-and-play capable tool is included on a reject list 618. Rejected tools may, for example, comprise tools of a type which are not supported by the robotic system, tools of a type which are no longer supported by any robotic system, or specific tools which have been identified, after distribution, as being unsuitable for use. Hence, tool rejection may be based on comparison of a tool type identifier or specific tool identifier with a reject list 522 in memory 516 of processor 502. Any tools or tool types included on reject list 522 will be rejected 620, with the system optionally providing an indication to the system operator and/or surgeon, the system inhibiting movement of the tool or insertion of the tool end effector into a patient, and the like.

If the loaded plug-and-play tool is not on the reject list, processor 502 may determine whether the system software of processor 502 is more up to date than the tool memory at step 622. This may be implemented by storing in the tool memory the most recent system processor software revision at the time a new tool is first ready for distribution. Any subsequent software revision will include the data for this new tool in the native list of the processor memory, so any system software revision that is more recent than the system revision information stored on the tool memory does not need to take advantage of the additional tool data stored on the tool memory. Effectively, this means that despite the tool memory and tool plug-and-play capabilities, the tool is treated like a known tool 512, and the additional tool data is obsolete. In method 600, if the processor determines that the additional tool data in the tool memory is obsolete at step 622, the tool is treated as a tool without plug-and-play capabilities. Note that the tool parametric information included in a subsequent system software revision may be different than (and more recent than) the additional tool data stored on the tool itself, so this avoids both delay in downloading additional tool information and use of obsolete tool information from the tool itself.

If the software revision of the processor does not postdate the additional tool data in the tool memory, the processor then checks whether the system has sufficient capabilities for using the tool in step 624. In some embodiments, this may be implemented by determining whether the current software revision of the processor is equal to or more recent than a minimum software revision specified in the tool memory. If not, the tool may have been designed to be used only by systems having, for example, software subroutines that are not currently available to the system processor.

The additional tool data will often comprise parametric data such as parametric link lengths, parametric maximum torque information, parametric range of motion information, and the like. If an entirely new type of kinematic assembly is included in a new tool, such parametric updating of the processor software may be insufficient absent a new subroutine. While it may be possible to load such new subroutines in a tool memory, limiting the additional tool data to parametric data limits the download time and hence tool swap delays.

In other embodiments, at step 624 the system may determine whether hardware capabilities of the system are sufficient to support the tool based on a comparison of minimum system capability information from the tool memory and actual system information for robotic system 502. For example, if an ultrasound surgical tool is intended to be mounted on robotic arms having ultrasound drivers, the incompatibility of the tool with the system capabilities may be identified in step 624. If the mounted tool is found to be incompatible with the system capabilities, method 600 determines whether the tool type is included in either the update list or the native list (possibly indicating that the incompatibility information in the tool memory is outdated), and if the tool type is not listed in either, the mounted tool is rejected in step 616.

Assuming that the processor of the system determines that the current software revision is not more recent than the information in the tool memory, and that the system has all capabilities required for proper use of the tool, the processor then determines whether the tool type of the mounted tool is already included on the update list in step 626. If the tool type is on the update list 520 of processor memory 516, the processor can use this existing additional tool data in its memory to support the instrument 610 without delaying for downloading of the additional tool data from the tool itself. Note that the update list of the processor memory may include additional tool data that is the same as the additional tool data on the tool, or may include more current additional tool data from a subsequently distributed tool of the same type having plug-and-play capabilities.

If the update list does not include the tool type of the loaded tool, or if the data of the loaded tool is more recent than the update list data for that tool type, the system processor goes on to check whether the native list 518 includes data which is more recent than (or as current as) the additional tool data from the tool memory in step 628. If the native list includes information for the tool type that is at least as current as the additional tool data from the tool memory, the system supports the mounted tool using the native list data. If current additional tool information is not already available in either the update list or the native list, the system processor directs downloading of the additional tool data into the update list 630.

In the exemplary embodiment, making use of tool data resident in the memory of processor 502 is the most rapid way to reconfigure the processor for a tool swap to a different tool type. Downloading of additional tool data from the memory of the tool will typically involve a delay of greater than one second, in some embodiments require a delay of greater than seconds, and in at least one embodiment a delay of about 14 seconds (depending on system state) as compared to making use of information already stored in a memory of the processor. Movement of a mounted tool is directed using six Sharc™ processors sold by ANALOG DEVICES of Massachusetts, ideally using a controller transform processor (CTP). Method 600 illustrating FIG. 7 is largely implemented using Middleman code, with the method being initiated by the Supervisor code data. Transferred data from a mounted tool is optionally preprocessed at circuitry of the slave robot arm. A wide variety of specific implementations may be employed within the scope of the present invention.

Figure 8:
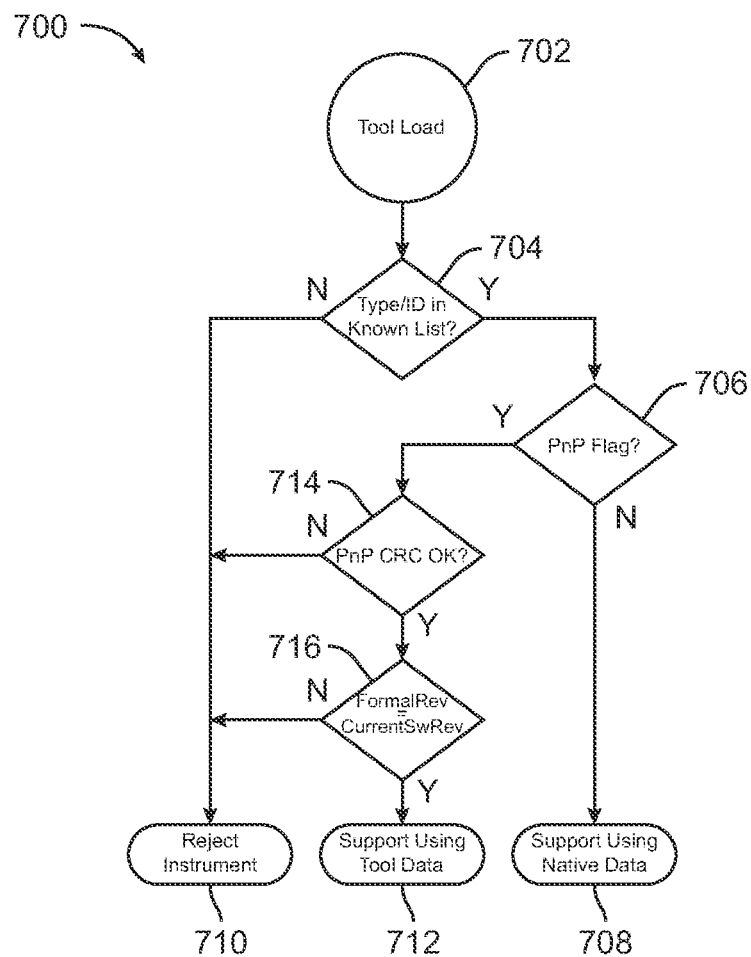
FIG. 8 is a flow chart illustrating program software embodying an alternative method for use of the system in FIG. 5.

Referring now to FIG. 8, some processors may not include all the capabilities of (or be employed in systems having all the need for) every aspect described above regarding method 600. In a simplified plug-and-play method 700, a tool is loaded onto a robotic arm and transmission of at least some of the data from a memory of the tool to a system processor is initiated so as to allow the processor to determine whether the tool type is included on a known tool list 704. If the tool type and/or tool identification is included on the known list, and if the tool is not plug-and-play capable 706, the tool can be supported using native data in the system processor 708.

If the processor determines 704 that the tool type is not on the known list, the processor may simply reject the instrument 710. Hence, the methods of the present invention may not necessarily be used to allow the use of new tool types. Instead, if the system processor determines that the tool is a known type but that the tool has plug-and-play capabilities, the processor may support the tool by downloading at least a portion of the additional tool information and using that downloaded information to configure the processor 712 if certain conditions are met. The exemplary system downloads limited PNP parameters of tool data 230, as seen in FIG. 6A. The processor may check that the downloaded data integrity appears acceptable by verifying a header stream (including the limited PNP data) in step 714. The processor may then verify that the current software revision of the processor is compatible with the tool per the downloaded additional tool data in step 716. If the tool integrity does not appear sufficient or the current software revision is not compatible, the tool is rejected. If the data integrity is acceptable and the software is compatible, the downloaded additional tool data from the memory of the tool is used to direct movement of the tool.

In simplified plug-and-play method 700, not all available additional tool information on the tool memory need necessarily be downloaded and/or used by the system. As mentioned above regarding FIG. 6A, the additional tool information may include limited PNP information 230. In the exemplary embodiment, the limited PNP information comprises a series of parameters. If the system has limited (rather than full or no) plug-n-play capabilities and a parameter is listed among the limited PNP data, the system will use the parameter from the tool update data (rather than that of the native list) by reconfiguring the processor software using that updated parameter. In the exemplary embodiment, the limited PNP data comprises parametric values for tool tip length, grip open torque, grip close torque, and grip angle.

A variety of alternative end effectors for alternative tools are illustrated in FIGS. 8A through 8F. Several of these end effectors, including DEBAKEY forceps 56i, microforceps 56ii, Potts scissors 56iii, and clip applier 56iv include first and second end effector elements 56a, 56b which pivot relative to each other so as to define a pair of end effector jaws. Other end effectors, including scalpel 56v and electrocautery probe 56vi have a single end effector element.

The tool data may optionally correlate to a limitation on an acceptable use for a specific mounted tool and/or a tool type. Tool and/or tool type identifiers may be stored on one or more tool use lists in the system memory, and the processor may alter or limit use of the tool in response to a comparison of a use list to the downloaded tool or tool type identifier. In some embodiments, the tool use data may be stored in the memory of the tool. Regardless, tool use restrictions may limit tools to training/demonstrations only, to engineering or prototype development, to clinical medical trials, or may allow use in surgery on humans. Tool life may vary with these different uses, and allowed use of a tool may change by revising the tool use data. Tool restrictions may be imposed by rejecting a non-allowed tool, by red or other appropriate icons shown in a display of the system, or the like.

While the exemplary embodiments have been described in detail, for clarity of understanding and by way of example, a variety of changes, adaptations, and modifications will be obvious to those of skill in the art. For example, while the exemplary embodiment is described with reference to changing robotic surgical tool kinematics and the like, alternative embodiments may facilitate the use of updated ultrasonic imaging probes with existing ultrasound system, alternative cardiac ablation catheters with a RF ablation system, or new robotic tools with an existing autonomous industrial robot. Hence, the scope of the present invention is limited solely by the appended claims.

What is claimed is:

1. A method comprising:
providing a plurality of systems, each system having a processor, to a plurality of customers;
distributing to the customers a plurality of limited-use devices, each device coupleable to one of the plurality of systems so as to perform a primary function; and
updating programming code or data of the processors from memories of the coupled devices so as to alter the performance of the primary function after the devices are decoupled from the systems;
each of said plurality of systems comprising a robotic surgical system having a processor and a robotic arm, each of said plurality of limited-use devices comprising a robotic tool mountable to a respective robotic arm.

2. The method of claim 1, said primary function comprising directing movement of each mounted robotic tool with the processor using data or code associated with the mounted robotic tool type.

3. The method of claim 1, said robotic tools having a plurality of different surgical end effectors, and wherein the movement of the surgical end effectors is directed by a surgeon moving an input device so as to perform a surgical procedure, the robotic arm and input device being components of a master-slave surgical robotic system.

4. The method of claim 1, each of said plurality of devices comprising a device identifier stored in a memory of the device.

5. The method of claim 4, each of said plurality of devices further comprising a revision identifier stored in said memory of the device, said updating comprising modifying the revision identifier.

6. The method of claim 5, wherein a memory of each processor stores a software revision identifier, each of said plurality of devices comprising a maximum software revision stored in a memory of the device, the processor directing movement of a coupled device using said updated programming code or data stored on the coupled device in response to the software revision identifier of the processor being older than the maximum software revision of the coupled device.

7. The method of claim 4, each of said plurality of devices further comprising a minimum system capability identifier stored in said memory of the device.

8. The method of claim 7, wherein said processors are configured to inhibit use of a device coupled to a corresponding system if a system capability of said processor is compatible with the minimum system capability identifier stored in said memory of the coupled device.

9. The method of claim 1, further comprising, prior to the providing the plurality of systems to the plurality of customers:
configuring each processor to store updated programming code or data downloaded from said memories of the coupled devices in an update list of a processor memory, the update list comprising downloaded data associated with a plurality of additional device types, the processor memory also comprising a native list of data associated with the types of the plurality of devices.

10. The method of claim 9, further comprising, prior to the providing the plurality of systems to the plurality of customers:
configuring each processor to, when performing said primary function, give priority to the downloaded data of the update list over the native list of data when a device identifier of a coupled tool is included in both the update list and the native list.

* * * * *